United States Patent
Green et al.

(10) Patent No.: US 10,675,164 B2
(45) Date of Patent: Jun. 9, 2020

(54) CATHETER HAVING DUAL BALLOON HYDRAULIC ACTUATOR

(71) Applicant: ABBOTT CARDIOVASCULAR SYSTEMS INC., Santa Clara, CA (US)

(72) Inventors: Michael L. Green, Pleasanton, CA (US); Michael R. Bialas, Wildomar, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 608 days.

(21) Appl. No.: 15/163,984

(22) Filed: May 25, 2016

(65) Prior Publication Data

US 2016/0262920 A1 Sep. 15, 2016

Related U.S. Application Data

(62) Division of application No. 13/467,679, filed on May 9, 2012, now abandoned.

(51) Int. Cl.
*A61F 2/966* (2013.01)
*A61M 25/09* (2006.01)
(Continued)

(52) U.S. Cl.
CPC .............. *A61F 2/966* (2013.01); *A61F 2/958* (2013.01); *A61M 25/09* (2013.01);
(Continued)

(58) Field of Classification Search
CPC .. A61F 2/966; A61F 2/958; A61F 2002/9522; A61M 25/10182;
(Continued)

(56) References Cited

U.S. PATENT DOCUMENTS 5,534,007 A   7/1996 St. Germain et al.
5,676,654 A   10/1997 Ellis et al.
(Continued)

FOREIGN PATENT DOCUMENTS

EP   1208816 A2   5/2002
JP   11-505162    5/1999

OTHER PUBLICATIONS

U.S. Appl. No. 13/467,679 (US 2013/0304180), filed May 9, 2012 (Nov. 14, 2013).
(Continued)

*Primary Examiner* — Jing Rui Ou
(74) *Attorney, Agent, or Firm* — Baker Botts L.L.P.

(57) ABSTRACT

Catheter comprising an inner tubular member defining a fluid lumen and inflation lumen therein. An exterior surface of the inner tubular member defines a fluid flow port in fluid communication with the fluid lumen and located along a region of the inner tubular member. Catheter further includes an outer member having a distal section movable relative to the inner tubular member and having an interior surface. A piston balloon is coupled to the inner tubular member distal to the fluid flow port and is in fluid communication with the inflation lumen. A pressure chamber is in fluid communication with the fluid flow port. Fluid introduced through the inflation lumen inflates the piston balloon to seal against the interior surface and fluid introduced through the fluid flow port and into the pressure chamber applies a force to urge at least the distal section of the outer member in a proximal direction.

29 Claims, 9 Drawing Sheets

(51) Int. Cl.
  *A61M 25/00* (2006.01)
  *A61F 2/95* (2013.01)
  *A61M 25/10* (2013.01)
  *A61F 2/958* (2013.01)
  *A61M 25/01* (2006.01)

(52) U.S. Cl.
  CPC .... *A61M 25/10182* (2013.11); *A61M 25/10185* (2013.11); *A61F 2002/9522* (2013.01); *A61M 2025/0079* (2013.01); *A61M 2025/0183* (2013.01); *A61M 2025/1079* (2013.01); *A61M 2025/1081* (2013.01)

(58) Field of Classification Search
  CPC ............ A61M 25/10185; A61M 25/09; A61M 2025/0079; A61M 2025/0183; A61M 2025/1079; A61M 2025/1081
  See application file for complete search history.

(56) References Cited

U.S. PATENT DOCUMENTS

| | | | |
|---|---|---|---|
| 5,695,468 A | 12/1997 | Lafontaine et al. | |
| 5,709,703 A | 1/1998 | Lukic et al. | |
| 5,776,141 A | 7/1998 | Klein et al. | |
| 5,817,101 A | 10/1998 | Fiedler | |
| 5,989,263 A * | 11/1999 | Shmulewitz | A61M 29/02 606/108 |
| 6,056,759 A | 5/2000 | Fiedler | |
| 6,059,813 A * | 5/2000 | Vrba | A61F 2/01 606/198 |
| 6,113,608 A | 9/2000 | Monroe et al. | |
| 6,214,037 B1 | 4/2001 | Mitchell et al. | |
| 6,287,285 B1 | 9/2001 | Michal et al. | |
| 6,425,898 B1 | 7/2002 | Wilson et al. | |
| 6,514,261 B1 | 2/2003 | Randall et al. | |
| 6,520,983 B1 | 2/2003 | Colgan et al. | |
| 6,541,116 B2 | 4/2003 | Michal et al. | |
| 6,605,109 B2 | 8/2003 | Fiedler | |
| 6,884,257 B1 | 4/2005 | Cox | |
| 6,942,682 B2 | 9/2005 | Vrba et al. | |
| 6,945,989 B1 | 9/2005 | Betelia et al. | |
| 7,163,552 B2 | 1/2007 | Diaz | |
| 7,632,296 B2 | 12/2009 | Malewicz | |
| 7,740,652 B2 | 6/2010 | Gerdts et al. | |
| 7,799,065 B2 | 9/2010 | Pappas | |
| 7,875,067 B2 | 1/2011 | Von Oepen | |
| 8,118,853 B2 | 2/2012 | Grewe | |
| 8,435,279 B2 | 5/2013 | Beyerlein et al. | |
| 8,652,198 B2 | 2/2014 | Andreas et al. | |
| 8,685,076 B2 | 4/2014 | Gerdts et al. | |
| 9,119,742 B2 | 9/2015 | Chuter et al. | |
| 9,283,101 B2 | 3/2016 | Shumer et al. | |
| 9,326,875 B2 | 5/2016 | Shumer et al. | |
| 2001/0027323 A1 | 10/2001 | Sullivan, III et al. | |
| 2001/0044630 A1 | 11/2001 | Stack et al. | |
| 2002/0009535 A1 | 1/2002 | Michal et al. | |
| 2002/0010420 A1* | 1/2002 | Bagaoisan | A61M 25/0009 604/103.11 |
| 2002/0026182 A1* | 2/2002 | Joye | A61B 18/02 606/21 |
| 2002/0045929 A1 | 4/2002 | Diaz | |
| 2002/0058951 A1 | 5/2002 | Fiedler | |
| 2002/0133118 A1 | 9/2002 | Gerdts et al. | |
| 2002/0165574 A1* | 11/2002 | Ressemann | A61B 17/12045 606/194 |
| 2003/0176910 A1* | 9/2003 | Vrba | A61F 2/01 623/1.11 |
| 2003/0187474 A1 | 10/2003 | Keegan et al. | |
| 2004/0143315 A1* | 7/2004 | Bruun | A61F 2/95 623/1.11 |
| 2004/0193178 A1 | 9/2004 | Nikolchev | |
| 2004/0193243 A1 | 9/2004 | Mangiardi et al. | |
| 2005/0149166 A1 | 7/2005 | Schaeffer et al. | |
| 2005/0209674 A1 | 9/2005 | Kutscher et al. | |
| 2005/0222557 A1 | 10/2005 | Baxter et al. | |
| 2006/0030923 A1 | 2/2006 | Gunderson | |
| 2006/0106366 A1 | 5/2006 | Wang | |
| 2006/0200191 A1 | 9/2006 | Zadno-Azizi | |
| 2006/0200221 A1* | 9/2006 | Malewicz | A61F 2/966 623/1.11 |
| 2007/0078506 A1 | 4/2007 | McCormick et al. | |
| 2007/0083188 A1* | 4/2007 | Grandt | A61M 25/10 604/524 |
| 2007/0100413 A1 | 5/2007 | Dwyer et al. | |
| 2007/0123971 A1 | 5/2007 | Kennedy et al. | |
| 2008/0118544 A1 | 5/2008 | Wang | |
| 2008/0125711 A1* | 5/2008 | Alpini | A61M 25/1002 604/103.06 |
| 2008/0294230 A1 | 11/2008 | Parker | |
| 2009/0018529 A1 | 1/2009 | Hoffman et al. | |
| 2009/0204197 A1 | 8/2009 | Dorn et al. | |
| 2009/0292262 A1 | 11/2009 | Adams et al. | |
| 2009/0312832 A1 | 12/2009 | Delap | |
| 2010/0087906 A1 | 4/2010 | Dorn et al. | |
| 2010/0286756 A1 | 11/2010 | Dorn et al. | |
| 2011/0112567 A1 | 5/2011 | Lenker et al. | |
| 2011/0307049 A1 | 12/2011 | Kao | |
| 2012/0148175 A1* | 6/2012 | Wesselmann | A61M 25/01 384/15 |
| 2013/0073024 A1 | 3/2013 | Russo et al. | |
| 2013/0138090 A1 | 5/2013 | Fargahi | |
| 2013/0297011 A1 | 11/2013 | Morris et al. | |
| 2013/0304179 A1* | 11/2013 | Bialas | A61F 2/966 623/1.11 |
| 2013/0304181 A1* | 11/2013 | Green | A61F 2/966 623/1.11 |
| 2014/0194969 A1 | 7/2014 | Headley | |
| 2014/0214151 A1 | 7/2014 | Ibeling | |
| 2014/0277356 A1 | 9/2014 | Shumer et al. | |

OTHER PUBLICATIONS

U.S. Appl. No. 13/467,660 (U.S. Pat. No. 9,011,513), filed May 9, 2012 (Apr. 21, 2015).
U.S. Appl. No. 13/467,715 (U.S. Pat. No. 9,271,855), filed May 9, 2012 (Mar. 1, 2016).
U.S. Appl. No. 13/797,636 (U.S. Pat. No. 9,283,101), filed Mar. 12, 2013 (Mar. 15, 2016).
U.S. Appl. No. 13/801,588 (U.S. Pat. No. 9,326,875), filed Mar. 13, 2013 (May 3, 2016).
U.S. Appl. No. 14/767,968 (US 2016/0051386), filed Aug. 14, 2015 (Feb. 25, 2016).
U.S. Appl. No. 14/653,582 (US 2016/0038321), filed Jun. 18, 2015 (Feb. 11, 2016).
U.S. Appl. No. 14/643,110 (US 2015/0245937), filed Mar. 10, 2015 (Sep. 3, 2015).
U.S. Appl. No. 13/467,660, Feb. 25, 2015 Issue Fee Payment.
U.S. Appl. No. 13/467,660, Nov. 25, 2014 Notice of Allowance.
U.S. Appl. No. 13/467,660, Oct. 14, 2014 Response after Final Action.
U.S. Appl. No. 13/467,660 Oct. 7, 2013 Non-Final Office Action.
U.S. Appl. No. 13/467,660, Jan. 7, 2014 Response to Non-Final Office Action.
U.S. Appl. No. 13/467,660, Jul. 17, 2014 Final Office Action.
U.S. Appl. No. 13/467,679, May 11, 2016 Response to Non-Final Office Action.
U.S. Appl. No. 13/467,679, Feb. 11, 2016 Non-Final Office Action.
U.S. Appl. No. 13/467,679, Oct. 14, 2014 Response to Restriction Requirement.
U.S. Appl. No. 13/467,679, Aug. 22, 2014 Restriction Requirement Filed.
U.S. Appl. No. 13/467,715, Jan. 20, 2016 Issue Fee Payment.
U.S. Appl. No. 13/467,715, Dec. 18, 2015 Notice of Allowance.
U.S. Appl. No. 13/467,715, Nov. 9, 2015 Response to Restriction Requirement.
U.S. Appl. No. 13/467,715, Sep. 9, 2015 Restriction Requirement Filed.
U.S. Appl. No. 13/797,636, Feb. 5, 2016 Issue Fee Payment.

(56) References Cited

OTHER PUBLICATIONS

U.S. Appl. No. 13/797,636, Dec. 10, 2015 Notice of Allowance.
U.S. Appl. No. 13/797,636, Oct. 30, 2015 Response to Non-Final Office Action.
U.S. Appl. No. 13/797,636, Jun. 30, 2015 Non-Final Office Action.
U.S. Appl. No. 13/801,588, Aug. 20, 2015 Non-Final Office Action.
U.S. Appl. No. 13/801,588, Jul. 9, 2015 Restriction Requirement Filed.
U.S. Appl. No. 13/801,588, Mar. 31, 2016 Issue Fee Payment.
U.S. Appl. No. 13/801,588, Feb. 1, 2016 Notice of Allowance.
U.S. Appl. No. 13/801,588, Jan. 22, 2016 Applicant Initiated Interview Summary.
U.S. Appl. No. 13/801,588, Nov. 19, 2015 Response to Non-Final Office Action.
U.S. Appl. No. 14/643,110, Feb. 29, 2016 Notice of Allowance.
U.S. Appl. No. 14/643,110, Oct. 30, 2015 Response to Non-Final Office Action.
U.S. Appl. No. 14/643,110, Jul. 30, 2015 Non-Final Office Action.
International Search Report and Written Opinion for PCT/US2013/036881, dated Aug. 2, 2013.
International Search Report and Written Opinion for PCT/US2013/036884, dated Aug. 2, 2013.
International Search Report and Written Opinion for PCT/US2013/030513, dated Aug. 2, 2013.
International Search Report and Written Opinion for PCT/US2013/069477, dated Jan. 8, 2014.
International Search Report for PCT/US2013/030830, dated Jan. 15, 2014.
International Search Report for PCT/US2013/068306, dated Jan. 8, 2014.
U.S. Appl. No. 13/467,679, Aug. 25, 2017 Notice of Abandonment.
U.S. Appl. No. 13/467,679, Apr. 24, 2017 Applicant Initiated Interview Summary.
U.S. Appl. No. 13/467,679, Feb. 9, 2017 Final Office Action.
U.S. Appl. No. 13/467,679, Nov. 22, 2016 Amendment and Request for Continued Examination (RCE).
U.S. Appl. No. 13/467,679, Aug. 22, 2016 Final Office Action.
U.S. Appl. No. 14/653,582, Nov. 14, 2017 Non-Final Office Action.
U.S. Appl. No. 14/653,582, Oct. 6, 2017 Response to Restriction Requirement.
U.S. Appl. No. 14/653,582, Aug. 14, 2017 Restriction Requirement.
U.S. Appl. No. 14/767,968, Nov. 30, 2017 Non-Final Office Action.
U.S. Appl. No. 15/180,655, Jan. 17, 2018 Notice of Allowance.
U.S. Appl. No. 15/180,655, Sep. 5, 2017 Response to Non-Final Office Action.
U.S. Appl. No. 15/180,655, May 2, 2017 Non-Final Office Action.
U.S. Appl. No. 15/180,655, filed Jun. 13, 2016.
U.S. Appl. No. 14/643,110, May 27, 2016 Issue Fee Payment.
U.S. Appl. No. 15/016,520, (US 2016/0151185), filed Feb. 5, 2016 (Jun. 2, 2016).

* cited by examiner

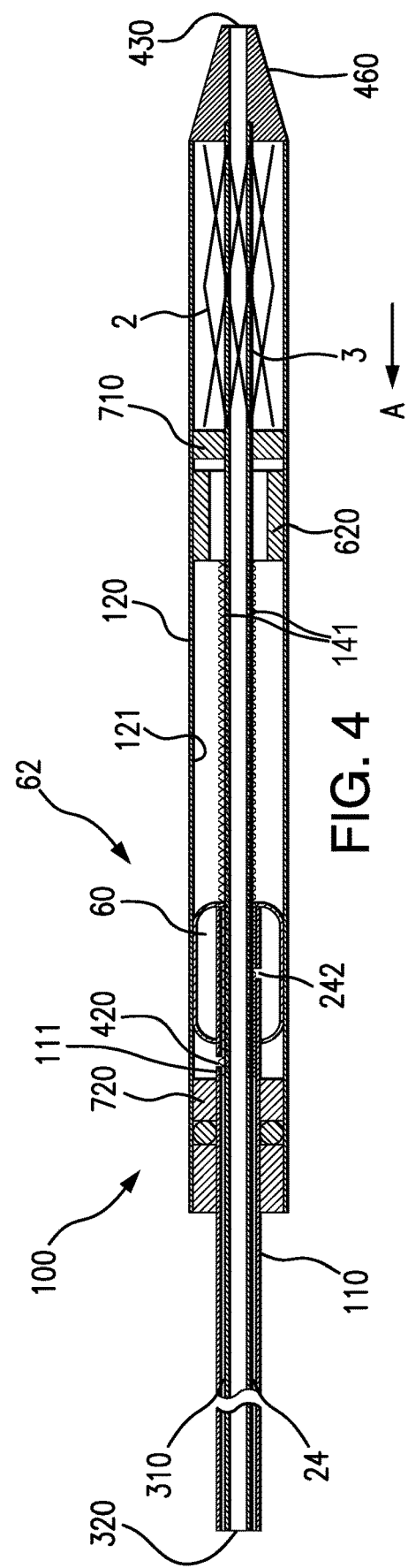

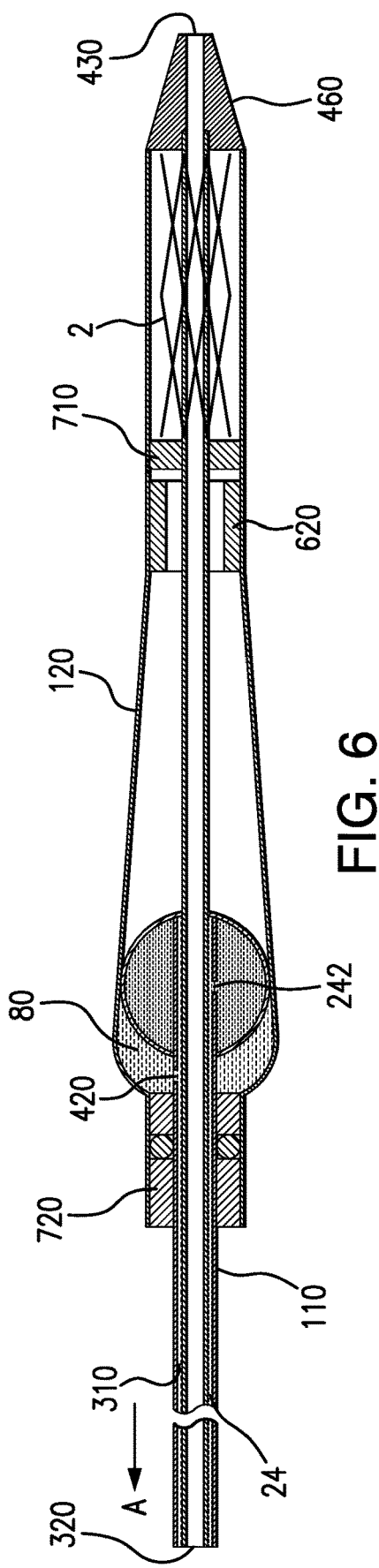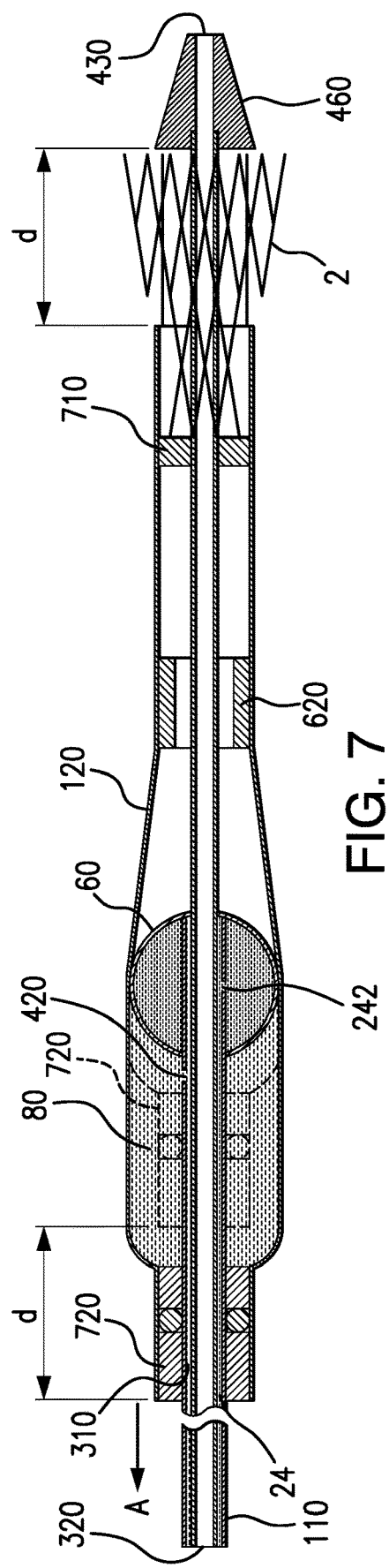

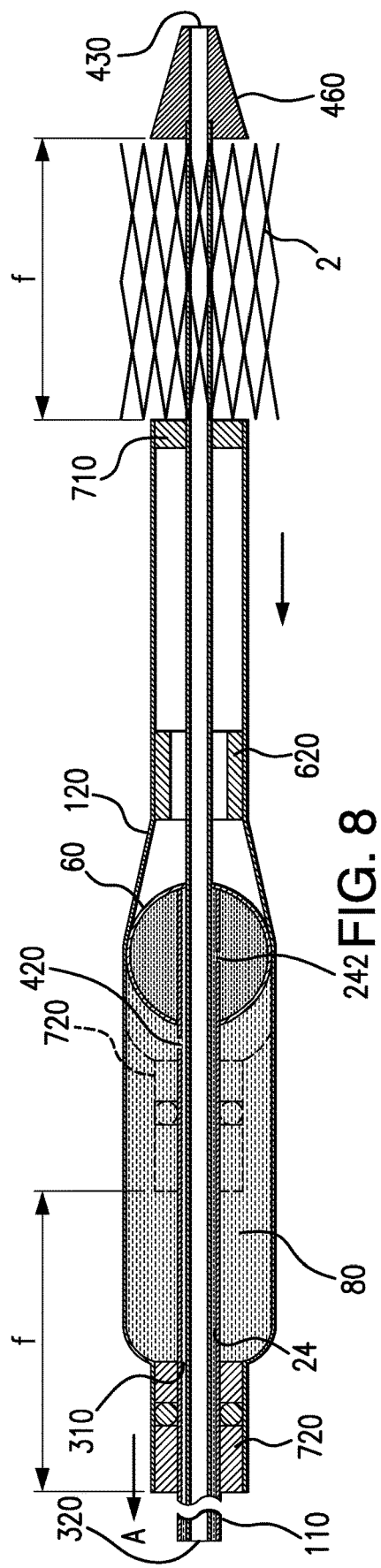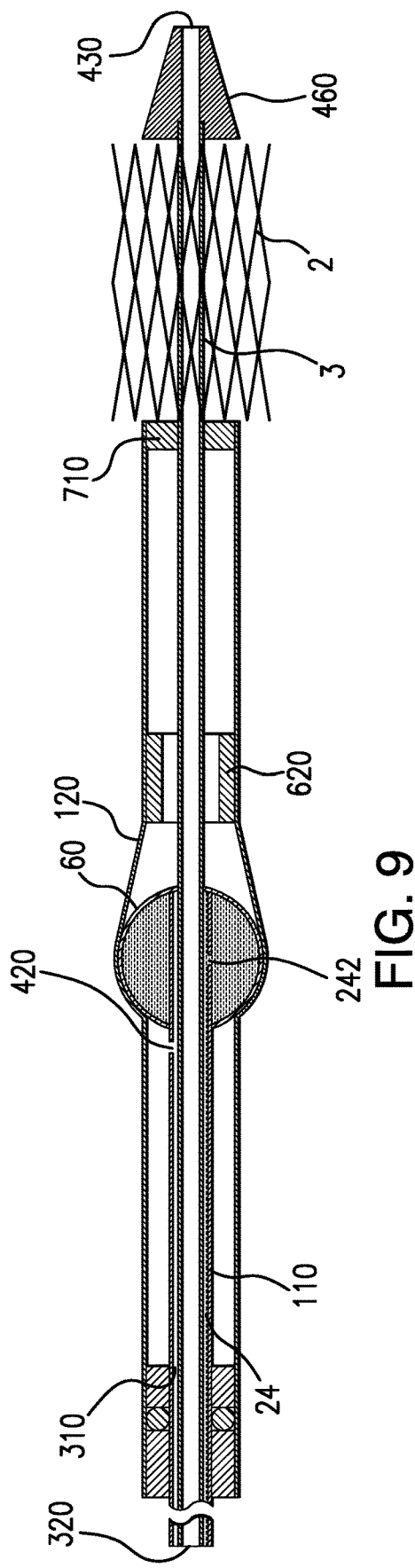

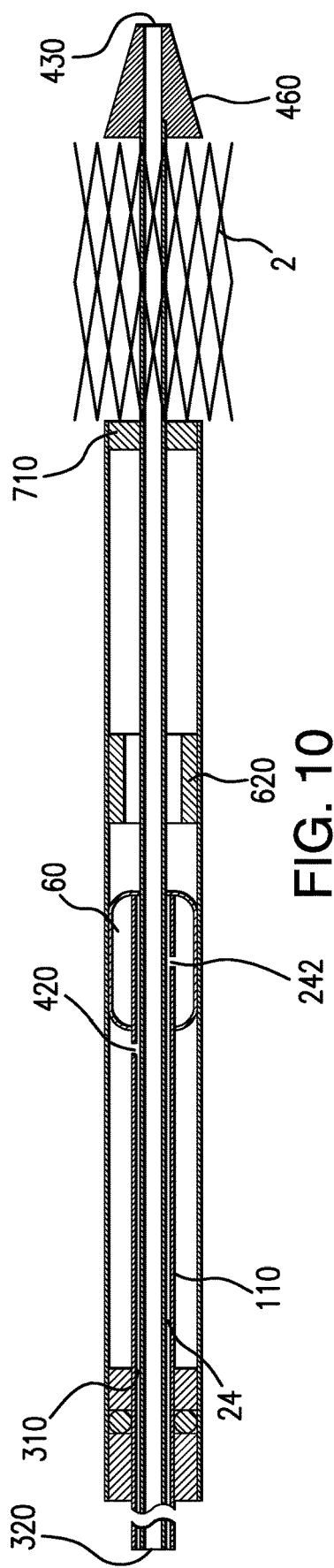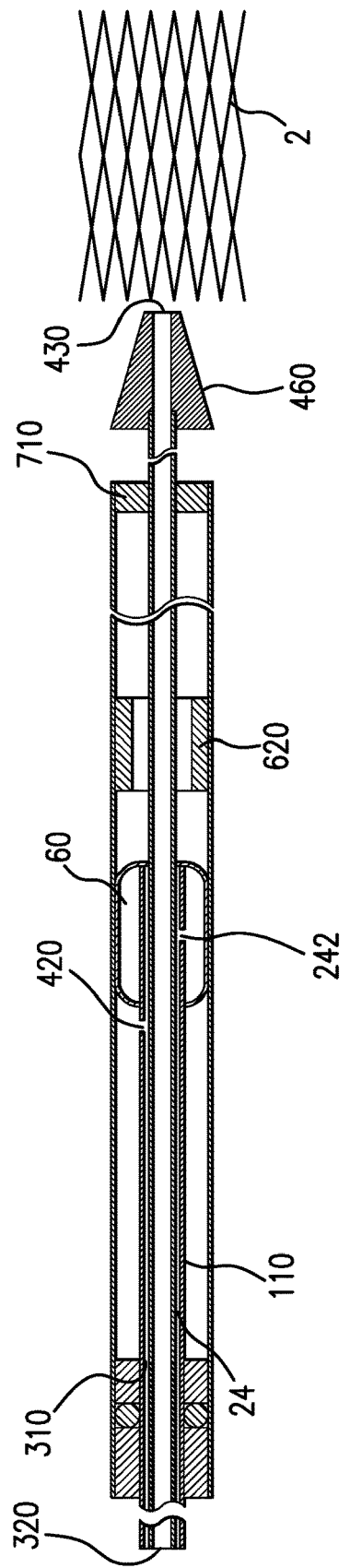

CATHETER HAVING DUAL BALLOON
HYDRAULIC ACTUATOR

CROSS-REFERENCE TO RELATED APPLICATION

This application is a divisional of U.S. patent application Ser. No. 13/467,679, filed on May 9, 2012, now abandoned, which is incorporated by reference herein in its entirety.

BACKGROUND OF THE DISCLOSED SUBJECT MATTER

Field of the Disclosed Subject Matter

The disclosed subject matter relates to catheters used in the delivery of medical devices, such as self-expanding stents, for treating the luminal systems of a patient. Specifically, the disclosed subject matter relates to a delivery catheter having a retractable sheath moved by a piston device.

Description of the Related Art

A variety of systems using a retractable sheath are known for intraluminal delivery of a medical device, such as a stent or filter. However, there remains a need for continued improvement of such known delivery systems.

An example of such a system is described in U.S. Pat. No. 6,425,898 to Wilson et al., which is incorporated by reference herein, wherein a delivery system is provided having an inner member with a stop attached to the inner member. During deployment, the stop prevents the stent from migrating proximally during retraction of the sheath for stent deployment.

Conventional self-expanding stent delivery systems generally comprise a handle portion and an elongated shaft, wherein the stent is disposed within a delivery portion at the distal end of the shaft. To deploy the stent, an outer sheath is provided which can be retracted relative to the stent to release the stent from its delivery configuration. The sheath in such systems generally spans the full length of the catheter resulting in an increased profile and stiffness over the entire length of the catheter. Further, because the sheath spans the full length of the catheter there is an increased risk of the sheath binding with other components of the catheter during passage through the tortuous luminal system of a patient, thus inhibiting the deployment of the stent.

Another issue with such delivery systems is that the sheath is generally pulled back in a 1-to-1 ratio with the user's input (force). Because the stent may embed in the outer sheath during storage and shipping, and due to larger static friction forces, a large amount of initial input is typically required to release the stent which may lead to incorrect placement. When initially releasing the stent, it may be desirable to slowly pull back the sheath for proper placement and then more readily retract the sheath to prevent inadvertent movement of the stent.

Further, the amount of force that is required to retract the sheath, particularly for stents of greater length as required for peripheral indications, can be substantial. Therefore there is a need for an improved delivery system for self-expanding stents having reduced force requirements for delivery of a self-expanding stent or the like.

There thus remains a continued need for an efficient and economic system for delivering a medical device that is easy to use and provides accurate placement. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a catheter comprising an inner tubular member having a length and an exterior surface, the inner tubular member defining a fluid lumen and an inflation lumen therein. The exterior surface defines a fluid flow port in fluid communication with the fluid lumen and located along a region of the inner tubular member. The catheter further includes an outer member having a distal section movable relative to the inner tubular member, the outer member having an interior surface facing the exterior surface of the inner tubular member. A piston balloon is coupled to the inner tubular member distal to the fluid flow port and is in fluid communication with the inflation lumen.

The piston balloon is disposed between the inner tubular member and the outer member and having a deflated condition and an inflated condition. The piston balloon in the inflated condition sealingly engages with the interior surface of the outer tubular member. A proximal seal is located proximal to the distal section and proximal to the fluid flow port. A pressure chamber is defined by the proximal seal, the piston balloon in the inflated position, the exterior surface of the inner tubular member, and the interior surface of outer member along the proximal section. The pressure chamber is in fluid communication with the fluid flow port. Fluid introduced through the inflation lumen inflates the piston balloon to seal against the interior surface of the outer member to define the pressure chamber and fluid introduced through the fluid flow port and into the pressure chamber applies a force to urge at least the distal section of the outer member in a proximal direction.

According to a further aspect of the disclosed subject matter, there is provided a catheter comprising an inner tubular member having a length and an exterior surface. The inner tubular member defines a lumen therein and the exterior surface defines a fluid flow port in fluid communication with the lumen and located along a region of the inner tubular member. The lumen further includes a directional control valve fluidly coupled with the fluid flow port wherein the directional control valve has a first position and a second position. An outer member having a distal section is movable relative to the inner tubular member. The outer member has an interior surface facing the exterior surface of the inner tubular member. A piston balloon is coupled to the inner tubular member and is in fluid communication with the fluid flow port.

The piston balloon is disposed between the inner tubular member and the outer member with the piston balloon having a deflated condition and an inflated condition. The piston balloon in the inflated condition sealingly engages with the interior surface of the outer tubular member. A proximal seal is located proximal to the distal section and proximal to the fluid flow port. The proximal seal extends from the interior surface of the outer member toward the exterior surface of the inner tubular member. A pressure chamber is defined by the proximal seal, the piston balloon in the inflated condition, the exterior surface of the inner tubular member, and interior surface of outer member along the proximal section. The pressure chamber is in fluid communication with the fluid flow port. The directional control valve in the first position channels fluid from the lumen through the fluid flow port to inflate the piston balloon to the extended position. The directional control valve engages to the second position to introduce fluid through the fluid flow port and into the pressure chamber to apply a force to urge the outer member in a proximal direction.

According to a further aspect of the disclosed subject matter, there is provided a catheter comprising an inner tubular member having a length and an exterior surface. The inner tubular member defines a lumen therein and the exterior surface defines a fluid flow port in fluid communication with the lumen and located along a region of the inner tubular member. The lumen further includes a directional control valve fluidly coupled with the fluid flow port wherein the directional control valve has a first position and a second position. An outer member having a distal section is movable relative to the inner tubular member. The outer member has an interior surface facing the exterior surface of the inner tubular member. A piston balloon is coupled to the inner tubular member and is in fluid communication with the fluid flow port. A marker is secured to the inner tubular member to seal a distal end of the fluid lumen distal of the fluid flow port. The proximal seal comprises at least one of hydrophilic material or molded hydrophilic material.

The piston balloon is disposed between the inner tubular member and the outer member and having a deflated condition and an inflated condition. The piston balloon in the inflated condition sealingly engages with the interior surface of the outer tubular member. A proximal seal is located proximal to the distal section and proximal to the fluid flow port. A pressure chamber is defined by the proximal seal, the piston balloon in the inflated position, the exterior surface of the inner tubular member, and the interior surface of outer member along the proximal section. The pressure chamber is in fluid communication with the fluid flow port. The method further includes inflating the piston balloon to the inflated condition by introducing inflation fluid through the inflation lumen and pressurizing the pressure chamber by introducing pressurizing fluid through the fluid flow port to apply a force on the proximal seal to urge the outer member in a proximal direction.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 4 is a schematic cross-sectional side view of a distal end of a representative embodiment of a catheter of the disclosed subject matter with the piston balloon in a deflated condition.

FIG. 6 is a schematic cross-sectional side view of the catheter of FIG. 5 with the piston balloon in the inflated condition and the pressure chamber initially filled with fluid.

FIG. 7 is a schematic cross-sectional side view of the catheter of FIG. 6 with the piston balloon in the inflated condition and the pressure chamber in a further expansion filled with fluid to urge the outer member in a proximal direction.

FIG. 8 is a schematic cross-sectional side view of the catheter of FIG. 7 depicting the outer member fully retracted and the deployment of the stent.

FIG. 9 is a schematic cross-sectional side view of the catheter of FIG. 8 with the stent deployed and the fluid from the pressure chamber withdrawn.

FIG. 10 is a schematic cross-sectional side view of the catheter of FIG. 9 with the fluid withdrawn from the piston balloon.

FIG. 11 is a schematic cross-sectional side view of the catheter of FIG. 10 depicting the withdrawal of the catheter from the stent.

DETAILED DESCRIPTION

Figure 1:
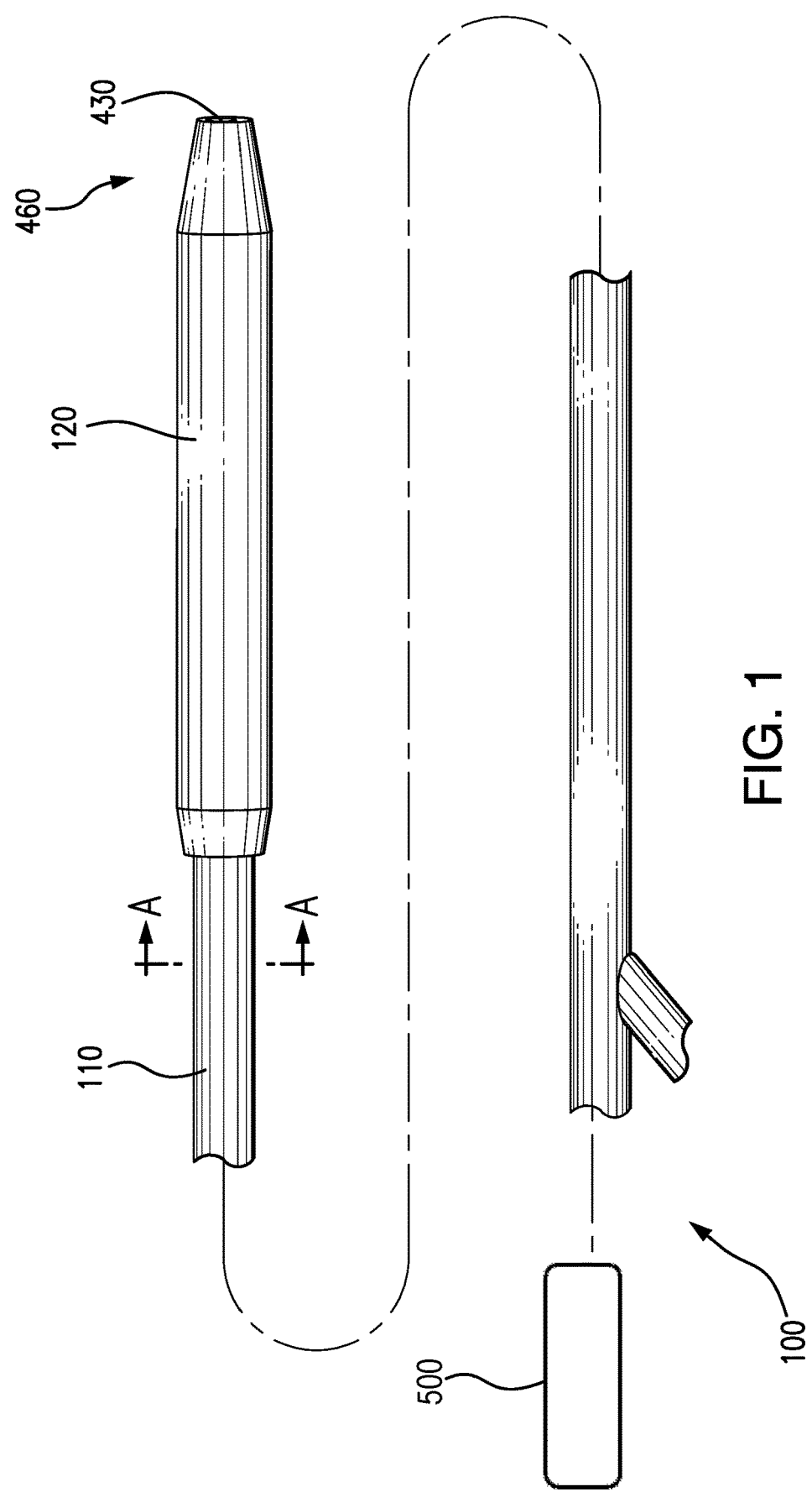
FIG. 1 is a schematic side view of a representative catheter in accordance with the disclosed subject matter.

Reference will now be made in detail to embodiments of the disclosed subject matter, an example of which is illustrated in the accompanying drawings. The disclosed subject matter will be described in conjunction with the detailed description of the system.

In accordance with the disclosed subject matter, a catheter is provided comprising an inner tubular member having a length and an exterior surface, the inner tubular member defining a fluid lumen and an inflation lumen therein. The exterior surface defines a fluid flow port in fluid communication with the fluid lumen and located along a region of the inner tubular member. The catheter further includes an outer member having a distal section movable relative to the inner tubular member, the outer member having an interior surface facing the exterior surface of the inner tubular member. A piston balloon is coupled to the inner tubular member distal to the fluid flow port and is in fluid communication with the inflation lumen.

The piston balloon is disposed between the inner tubular member and the outer member and having a deflated condition and an inflated condition. The piston balloon in the inflated condition sealingly engages with the interior surface of the outer tubular member. A proximal seal is located proximal to the distal section and proximal to the fluid flow port. A pressure chamber is defined by the proximal seal, the piston balloon in the inflated position, the exterior surface of the inner tubular member, and the interior surface of outer member along the proximal section. The pressure chamber is in fluid communication with the fluid flow port. Fluid introduced through the inflation lumen inflates the piston balloon to seal against the interior surface of the outer member to define the pressure chamber and fluid introduced through the fluid flow port and into the pressure chamber applies a force to urge at least the distal section of the outer member in a proximal direction.

According to a further aspect of the disclosed subject matter, there is provided a catheter comprising an inner tubular member having a length and an exterior surface. The inner tubular member defines a lumen therein and the exterior surface defines a fluid flow port in fluid communication with the lumen and located along a region of the inner tubular member. The lumen further includes a directional control valve fluidly coupled with the fluid flow port wherein the directional control valve has a first position and a second position. An outer member having a distal section is movable relative to the inner tubular member. The outer member has an interior surface facing the exterior surface of the inner tubular member. A piston balloon is coupled to the inner tubular member and is in fluid communication with the fluid flow port.

The piston balloon is disposed between the inner tubular member and the outer member with the piston balloon having a deflated condition and an inflated condition. The piston balloon in the inflated condition sealingly engages with the interior surface of the outer tubular member. A proximal seal is located proximal to the distal section and proximal to the fluid flow port. The proximal seal extends from the interior surface of the outer member toward the exterior surface of the inner tubular member. A pressure chamber is defined by the proximal seal, the piston balloon in the inflated condition, the exterior surface of the inner tubular member, and interior surface of outer member along the proximal section. The pressure chamber is in fluid communication with the fluid flow port. The directional control valve in the first position channels fluid from the lumen through the fluid flow port to inflate the piston balloon to the extended position. The directional control valve engages to the second position to introduce fluid through the fluid flow port and into the pressure chamber to apply a force to urge the outer member in a proximal direction.

According to yet another aspect of the disclosed subject matter, there is provided a method of deploying a catheter, comprising, providing a catheter comprising an inner tubular member having a length and an exterior surface, the inner tubular member defining a fluid lumen and an inflation lumen therein. The exterior surface defines a fluid flow port in fluid communication with the fluid lumen and located along a region of the inner tubular member. The catheter further includes an outer member having a distal section movable relative to the inner tubular member, the outer member having an interior surface facing the exterior surface of the inner tubular member. A piston balloon is coupled to the inner tubular member distal to the fluid flow port and is in fluid communication with the inflation lumen.

The piston balloon is disposed between the inner tubular member and the outer member and having a deflated condition and an inflated condition. The piston balloon in the inflated condition sealingly engages with the interior surface of the outer tubular member. A proximal seal is located proximal to the distal section and proximal to the fluid flow port. A pressure chamber is defined by the proximal seal, the piston balloon in the inflated position, the exterior surface of the inner tubular member, and the interior surface of outer member along the proximal section. The pressure chamber is in fluid communication with the fluid flow port. The method further includes inflating the piston balloon to the inflated condition by introducing inflation fluid through the inflation lumen and pressurizing the pressure chamber by introducing pressurizing fluid through the fluid flow port to apply a force on the proximal seal to urge the outer member in a proximal direction.

As disclosed herein, the device presented herein can be used for treating the luminal system of a patient. In particular, the disclosed subject matter is particularly suited for treatment of the cardiovascular system of a patient, such as delivery of a medical device into the vasculature. The catheter and method of the disclosed subject matter will be described in further detail and in conjunction with each other.

Solely for purpose of illustration, reference will now be made in detail to specific embodiments, examples of which are illustrated in the accompanying drawings. The examples are not intended to limit the scope of the disclosed subject matter in any manner. For the purposes of this disclosure, like reference numbers in the drawings shall refer to like features unless otherwise indicated.

Solely for purpose of illustration, FIG. 1 illustrates a representative embodiment of a catheter having a hydraulic delivery system for a medical device, at least a portion of which can be delivered within a vasculature or other body lumen, as shown schematically in the accompanying figures. The catheter 100 generally comprises an inner tubular member 110 having a length and an exterior surface, wherein the inner tubular member defines a fluid lumen and an inflation lumen therein, as further discussed below.

The inner tubular member 110 of the catheter 100 can include a variety of suitable configurations. For example, the inner tubular member can comprise an over the wire (OTW) configuration with a guidewire lumen extending generally the entire length of the inner tubular member or can comprise a rapid exchange configuration (RX) with a guidewire lumen extending from a proximal guidewire port to a distal end as generally known to one of skill in the art. In either the OTW or the RX configurations, the inner tubular member can furthermore have a co-axial arrangement or a multi-lumen arrangement.

Figure 2A:
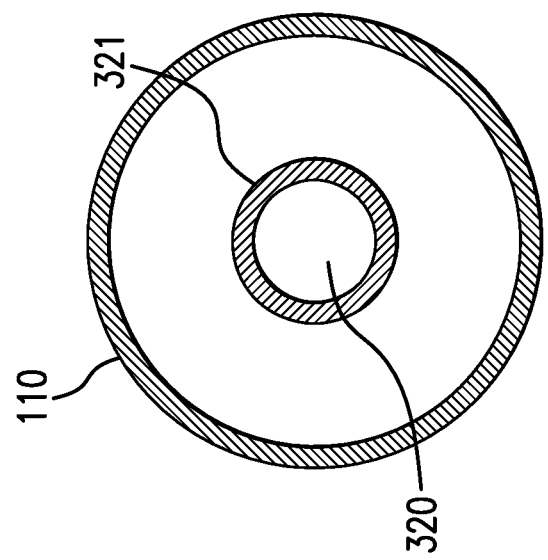

Solely for purpose of illustration, FIG. 2A depicts a representative cross-sectional view of a co-axial arrangement along lines A-A of FIG. 1. The co-axial arrangement includes an inner tubular member 110 and a guidewire tube 321 disposed therein. The guidewire tube 321 defines a guidewire lumen 320 therethrough. In this embodiment, a single lumen is defined in the annular space between the inner tubular member 110 and the guidewire tube 321. As described in detail herein, the single lumen can define both a fluid lumen and an inflation lumen in accordance with the disclosed subject matter. Furthermore, the guidewire lumen can be omitted if a proximal seal and a distal seal are provided and configured to allow a guidewire to extend therethrough. The inner tubular member 110 can be a single tube or an assembly of components coupled together along its length.

Figure 3A:
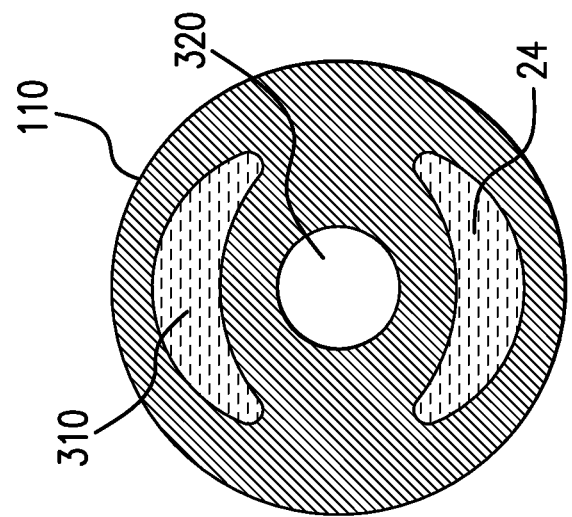
FIGS. 2A and 3A are cross-sectional views of different embodiments of the inner tubular member depicting a coaxial configuration and a multi-lumen configuration, respectively, taken along the lines A-A of FIG. 1, according to embodiments of the disclosed subject matter.

Alternately, FIG. 3A depicts a representative cross-sectional view of a multi-lumen arrangement. Solely for purpose of illustration, the inner tubular member 110 can be a monolithic member with a multi-lumen configuration. In such embodiment, the inner tubular member 110 defines an inflation lumen 24, a guidewire lumen 320, and a fluid lumen 310 therein. Solely for purpose of illustration, a monolithic multi-lumen inner tubular member 110 is also shown schematically in FIGS. 4-11. The inner tubular member 110 has a proximal end portion, a distal end portion, and a length. As depicted in FIGS. 4-11, the guidewire lumen 320 extends along at least a distal end portion of the inner tubular member, whereas the fluid lumen 310 and the inflation lumen 24 are defined at least along a portion of the proximal end portion therein.

With reference to FIGS. 4-11, the guidewire lumen 320 is configured to receive a guidewire for delivery of the catheter 100 through tortuous pathways of a vasculature or other body lumen. In an OTW catheter, the guidewire lumen 320 extends along the length of the catheter 100. In an RX catheter, the guidewire lumen 320 extends along a portion of the length of the catheter along a distal end portion of the inner tubular member. The guidewire lumen 320 includes a proximal guidewire port at a proximal end of the guidewire lumen (not shown). The location of the proximal guidewire port along the length of the inner tubular member will depend on whether the catheter is an OTW catheter or an RX catheter, as is known. The guidewire lumen has a distal guidewire port 430 at a distal end of the catheter 100. For example, and as embodied herein, the catheter 100 has a distal tip 460 at the distal end to define the distal guidewire port 430, as shown in FIG. 4. The distal tip 460 can further define the distal end for a stent seat 3 or the like, as described further below.

Alternatively, and in lieu of a separate guidewire lumen defined within the monolithic inner tubular member, a separate guidewire tube can be disposed in either the fluid lumen or the inflation lumen. In a further embodiment, the separate guidewire lumen can be omitted if either the fluid lumen or the inflation lumen includes a seal assembly configured to receive a guidewire therethrough.

As depicted in FIG. 4, and as previously noted, the inner tubular member 110 further defines a fluid lumen 310 and an inflation lumen 24 therein. The exterior surface 111 of the inner tubular member 110 defines a fluid flow port 420 in fluid communication with the fluid lumen 310 and located along a region of the inner tubular member. Fluid from an external source (not shown) therefore can be introduced through the fluid lumen 310 and exit though the fluid flow port 420.

As depicted in FIGS. 4-11, the exterior surface 111 of the inner tubular member 110 further defines the inflation port 242 or the like in fluid communication with the inflation lumen 24. The fluid flow port 420 and the inflation port 242 therefore define access points for fluid to exit the fluid lumen 310 and the inflation lumen 24, respectively. An adapter (not shown) is provided at the proximal end of the catheter for access to the inflation lumen 24 and the fluid lumen 310, respectively. The adapter can be configured to connect a fluid source (not shown) to the inflation lumen 24 and the fluid lumen 310, respectively. A conventional device, such as but not limited to an indeflator or a syringe, can introduce the fluid to the inflation lumen and fluid lumen, respectively, as described further below.

In an alternate embodiment and as previously noted, the fluid lumen 310 and the inflation lumen 24 can be combined and comprise a single shared lumen. FIG. 2A depicts an example of a cross-section of the inner tubular member 110 with a co-axial arrangement adapted for a single shared lumen. The guidewire lumen is positioned within the shared lumen, as provided in FIG. 2A. Such coaxial configurations allow for reduced diameter of the inner tubular member 110, and thus reduced profile. Further, the guidewire lumen can be formed by a thin membrane of suitable strength to prevent the guidewire from penetrating therethrough. For the co-axial arrangement the single shared lumen, fluid can be introduced annularly between the guidewire tube 321 and the inner tubular member 110 and thus outside the guidewire lumen 320.

Figure 12:
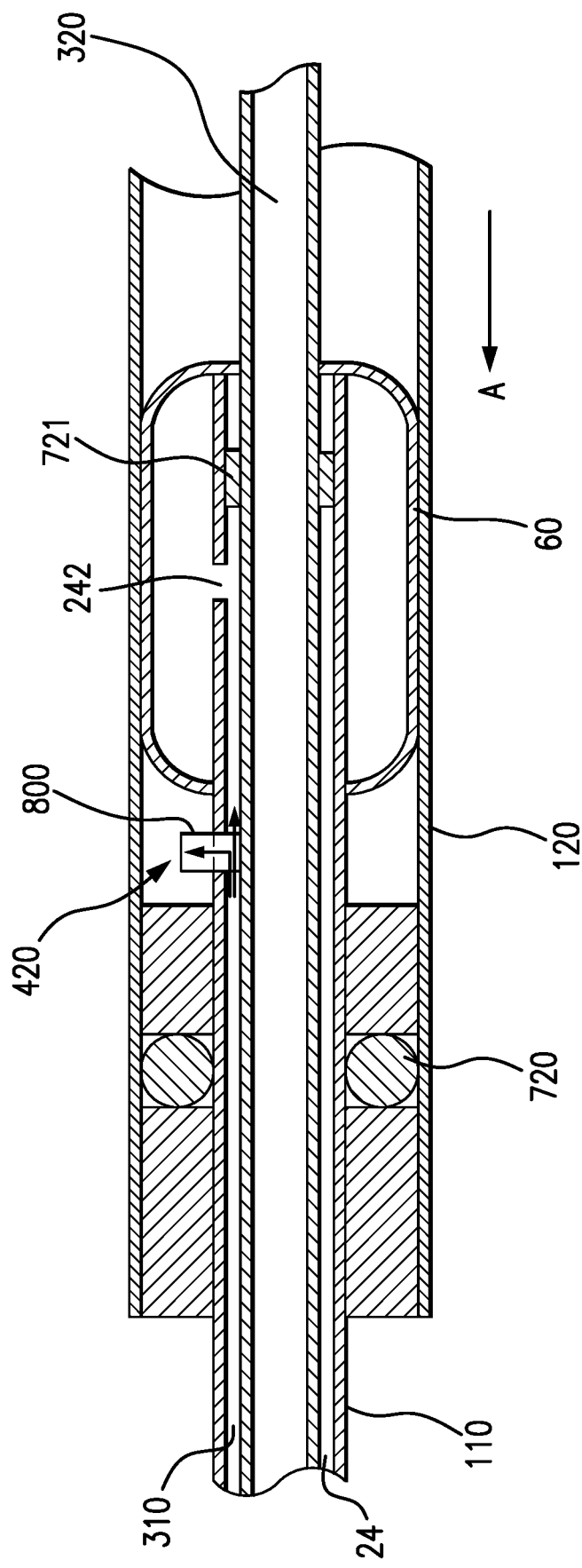
FIG. 12 is an enlarged cross-sectional side view of another representative embodiment of the catheter of the disclosed subject matter with a directional flow valve.

With reference again to FIGS. 4-11, the fluid flow port 420 and the inflation port 242 are located along the inner tubular member 110 at different locations, as previously described. Solely for purpose of illustration, FIG. 12 depicts an enlarged schematic view of the fluid flow port 420 and the inflation port 242 for a co-axial configuration. A seal or stop 721 is provided distal to the inflation port 242 to prevent fluid in the fluid lumen from flowing further distally. The stop 721 allows the guidewire to continue in the guidewire lumen 320.

In accordance with another aspect of the disclosed subject matter as depicted in FIG. 12, a directional control valve 800 or the like can be provided. For example, and as embodied herein with reference to the co-axial arrangement of FIG. 12, a directional control valve 800 or a suitable valve or seal is provided for selective operation to direct fluid through the fluid flow port 420 or inflation port 242 or both. The directional control valve 800 allows the fluid initially to bypass the fluid flow port 420 and to discharge or exit from the inflation port 242. Upon selective operation, such as when a predetermined flow or pressure is reach or by remote activation, the directional control valve 800 can redirect the fluid in the lumen to exit the fluid flow port 420, as depicted in FIG. 12. Similarly, and as described further herein, the directional control valve 800 controls the sequence in which fluid is withdrawn through the fluid port 420 and the inflation port 242, respectively.

As depicted in FIGS. 4-11 and as previously noted, the catheter further includes an outer member or sheath 120 having a distal section moveable relative to the inner tubular member 110. The outer member 120 has a proximal section, a distal section, and an interior surface 121. The inner tubular member 110 is positioned within the outer member 120 at least at the distal section of the catheter 100. As such, the exterior surface 111 of the inner tubular member 110 is directed toward the interior surface 121 of the outer member 120. With reference to FIG. 4, the outer member 120 is movable relative to the inner tubular member 110, such that the distal section of the outer member 120 can be retracted in a proximal direction A toward the proximal end of the catheter. As further shown in FIG. 4, the outer member 120 is disposed only at the distal end portion of the catheter 100, although the outer member can extend a greater length of the inner tubular member, if needed.

Figure 5:
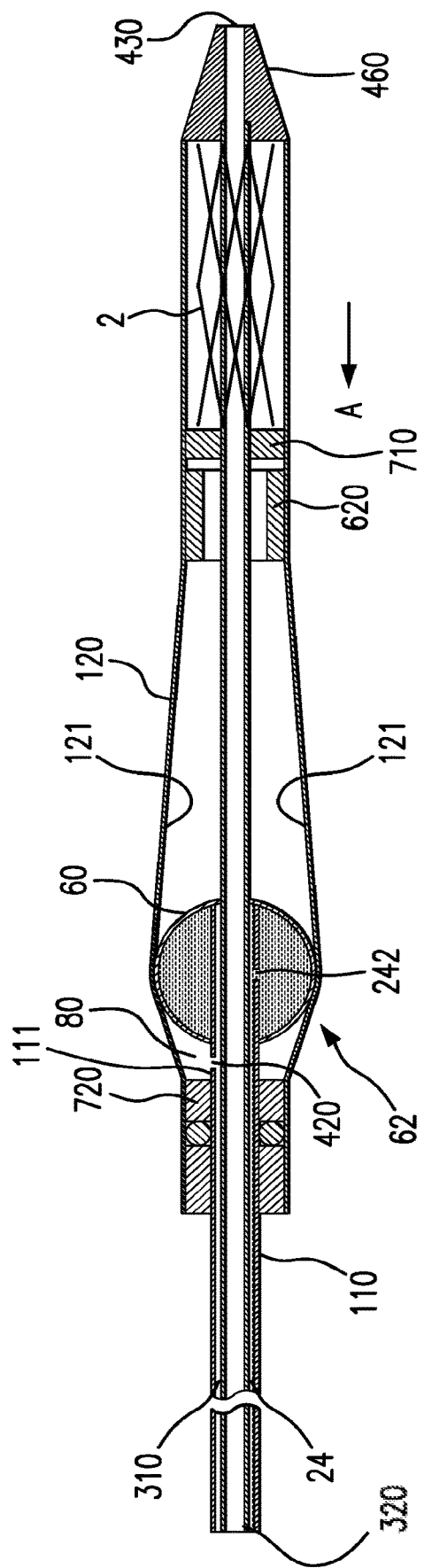
FIG. 5 is a schematic cross-sectional side view of the catheter of FIG. 4 with the piston balloon in an inflated condition.

As depicted in FIGS. 4-11 and as previously noted, the catheter further includes a piston balloon 60 coupled to the inner tubular member 110 distal to the fluid flow port 420 and in communication with the inflation lumen 242. The piston balloon 60 is disposed between the inner tubular member 110 and the outer member 120 for engagement with outer member 120. The piston balloon 60 has a deflated condition and an inflated condition, as depicted schematically in FIGS. 4 and 5, respectively. When in the inflated condition as depicted in FIG. 5, the piston balloon 60 is in sealing engagement with the interior surface 121 of the outer member 120.

As shown in FIG. 4, the piston balloon 60 is coupled to the inner tubular member 110 distal to the fluid flow port 420. The piston balloon 60 is in fluid communication with the inflation lumen 24, such as via the inflation port 242 as embodied herein. Fluid therefore can be introduced into the inflation lumen 24 at the proximal end of the catheter 100 and exit through the inflation port 242 to inflate the piston balloon 60. The piston balloon 60 is secured in a fixed location on the inner tubular member 110. As the piston balloon 60 inflates, the outer member 120 can be configured or formed of a suitable material to increase in diameter to maintain a seal against the piston balloon while still permitting axial movement of the outer member 120 thereacross. The piston balloon 60 can comprise suitable materials, for example, but not limited to, Pebax or Nylon, and/or a non-compliant material, as further discussed herein.

Additionally and with reference to the embodiment of FIG. 4, the catheter 100 includes a proximal seal 720 located proximal to the distal section of the outer member 120 and proximal to the fluid flow port 420. Particularly, the proximal seal defines in part a pressure chamber proximal to the piston balloon. For example, the proximal seal 720 can extend from the interior surface 121 of the outer member 120 toward the exterior surface 111 of the inner tubular member 110. The proximal seal 720 is located proximal to fluid flow port 420. The proximal seal 720 is fixed to the interior surface 121 of the outer member 120 and moves freely relative with respect to the inner tubular member 110. The movement of the proximal seal 720 in the proximal direction A, such as upon application of a force as described further below, effectuates the movement at least of the distal section of the outer member 120. A distal seal 620 can also be provided at a location distal to the piston balloon 60. The distal seal 620 embodied herein extends from the interior surface 121 of the outer member 120 toward the exterior surface 111 of the inner tubular member 110. The distal seal 620 is fixed to the interior surface 121 of the outer member 120 and moves freely relative with respect to the inner tubular member 110.

As such, and as embodied herein, a pressure chamber 80 is defined by the proximal seal 720, the piston balloon 60, the exterior surface 111 of the inner tubular member 110, and the interior surface 121 of outer member 120. The pressure chamber 80 is in fluid communication with the fluid flow port 420. As the pressure chamber 80 is pressurized by the introduction of fluid through the fluid flow port 420, the proximal seal 720 moves in the proximal direction A to thus urge at least the distal section of the outer member 120 in the proximal direction A.

In operation and as shown in FIG. 5, when the piston balloon 60 is in the inflated condition, pressurized fluid is introduced into the fluid lumen 310 and exits through the fluid flow port 420 into the pressure chamber 80. Once sufficient fluid is introduced into the pressure chamber 80 as shown in FIG. 6, the pressure chamber 80 pressurizes and an axially directed force is applied on the proximal seal 720 and the inflated piston balloon 60. Since the inflated balloon 60 is locally fixed to the inner tubular member 110 and the proximal seal 720 is moveable proximally, the generated force moves the proximal seal 720 in the proximal direction A. Since the proximal seal 720 of this embodiment is coupled to the outer member 120, the distal section of the outer member 120 is likewise moved in the proximal direction A, generally proportional with the proximal seal 720. The proximal seal 720, and thus the outer member 120, will continue to move in the proximal direction A until the force F is no longer generated.

Alternatively or in addition thereto as shown in FIGS. 8-11, the outer member 120 moves in the proximal direction A until a stop 710 comes into engagement with the distal end of the outer member 120. Such pressure can be controlled externally, for example, by a suitable indeflator or pressure source with locking mechanism to control the resulting force acting on the proximal seal, as further discussed herein.

Figure 13:
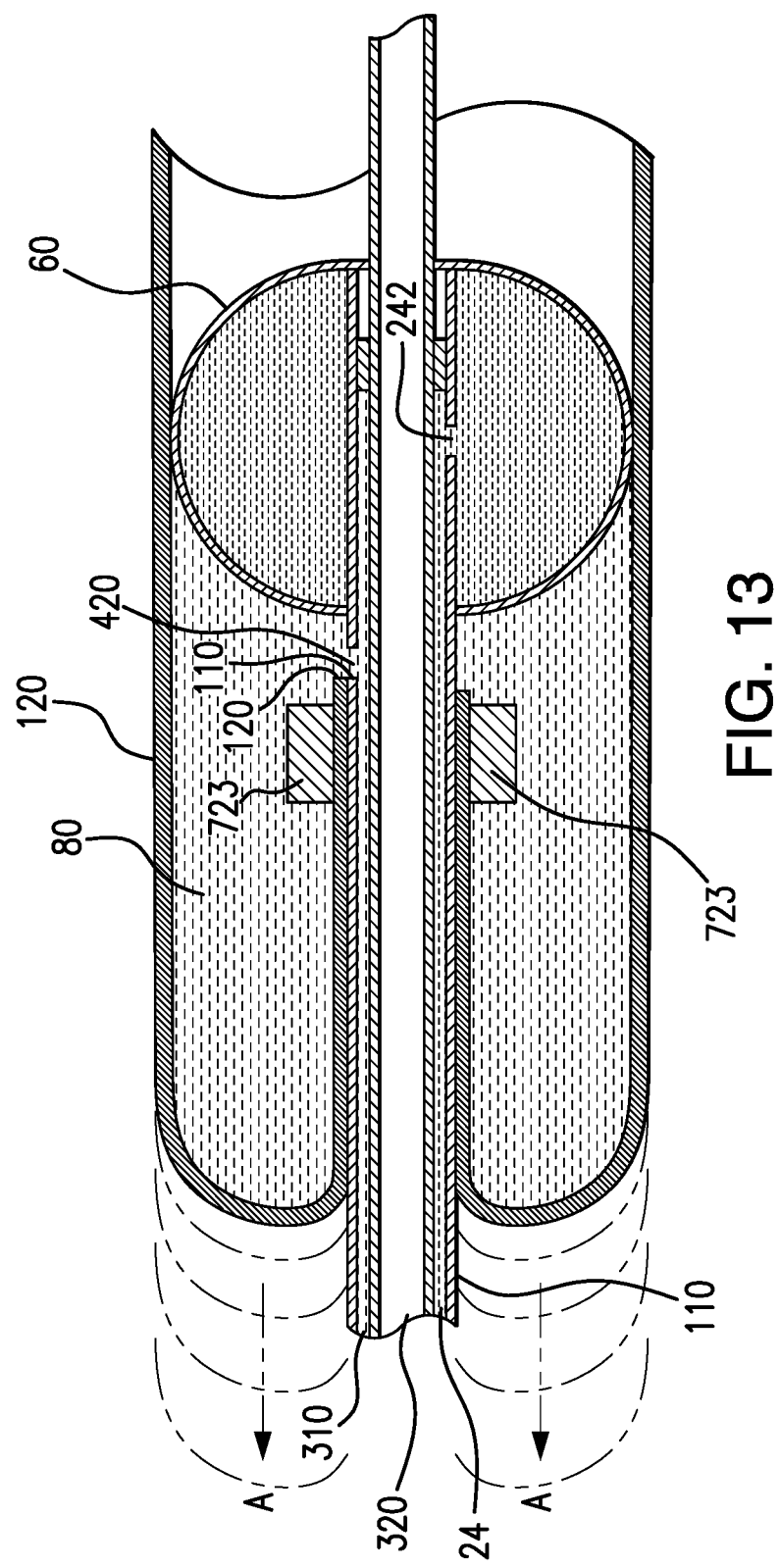
FIG. 13 is an enlarged cross-sectional side view of another representative embodiment of the catheter of the disclosed subject matter when the proximal end of the outer member sealingly coupled to the inner tubular member to form the proximal seal, and the piston balloon in an inflated condition and the pressure chamber filled with fluid.

With reference to FIG. 13 and in accordance with the disclosed subject matter, alternative arrangements can be used for the proximal seal to define the pressure chamber 80. For example, and in lieu of a movable proximal seal as previously discussed, the proximal end of the outer member 120 can alternatively be sealingly coupled with the inner tubular member 110. Solely for purpose of example, the proximal end of the outer member 120 can be secured directly to the inner tubular member 110 in a manner to allow outer member 120 to invert in on the proximal direction A. Alternatively, the proximal end of the outer member 120 can be heat bonded to the inner tubular member 110. In another arrangement, the proximal end of the outer member 120 can be bonded to the inner tubular member 110 with a suitable adhesive. Solely for purpose of illustration as depicted in FIG. 13, a collar 723 can be provided to secure the proximal end of the outer member 120 to the inner tubular member 110 in a fixed position. The collar 723 is secured to the inner tubular member 110 at a location proximal to the fluid flow port 420. The collar 723 thus forms a proximal seal for a pressure chamber 80, as depicted in FIG. 13. As the pressure chamber 80 is pressurized by fluid exiting the fluid flow port 420, the outer member 120 inverts in the proximal direction A as depicted in the phantom lines of FIG. 13. In this manner, the distal section of the outer member 120 will be drawn or move in the proximal direction A to expose a distal end of the inner tubular member 110. The collar 723 can be made of a suitable material, for example, a polymer heat-shrink tubing adapted to compress onto the inner tubular member. Suitable materials capable for an inverting outer member adapted to seal with the piston balloon and invert as described include, but are not limited to, pebax, nylon, polyethylene, or some combinations thereof. Alternative proximal seals likewise can be used or formed to define a pressure chamber 80 suitable to move or retract at least the distal section of the outer member 120, in accordance with the subject matter disclosed herein.

In accordance with another aspect of the disclosed subject matter, the pressure chamber 80 can be configured to increase in cross section when pressurized, such that a greater force is generated on the proximal end of the pressure chamber 80 due to the increased surface area. For example, the proximal section of the outer member 120 can be constructed to expand as it is pressurized, yet the distal section can be configured to maintain adequate hoop strength to retain the constrained stent or the like until retracted.

To accommodate relatively high fluid pressures to retract outer member 120, the pressure chamber 80 is formed to withstand such pressures with minimal leakage. A variety of suitable seal constructions and materials for the embodiments herein described can be used, such as, but not limited to, sliding seals, rings, cups seals, lips seals, and compressed bushings. For example each seal can be formed as a separate member and attached to the corresponding member, or can be formed as part of the tubular member, as further discussed herein.

In accordance with another aspect of the disclosed subject matter, and as embodied herein, for purposes of discussion, a seat or similar platform can be defined distal to the piston balloon for delivery of a medical device. For example, and as depicted in FIG. 4, the catheter 100 can include a medical device, such as a stent 2, positioned at the stent seat 3 between the inner tubular member 110 and the outer member 120 at the distal end of the catheter 100. When initially in its extended position as shown in FIG. 4, the outer member 120 retains the stent 2 in a compressed or delivery condition. When the distal section of outer member 120 is retracted as shown in FIGS. 5-11, the stent 2 is allowed to expand to its deployed condition, further discussed below. The self-expanding stent 2 is exposed by the movement of the outer member or sheath 120 in the proximal direction A. As described further herein, the catheter of the disclosed subject matter can be configured to deliver a medical device, such as the stent 2, of any suitable length. That is, the catheter 100 can be configured to generate a force sufficient to retract the outer tubular member 120, wherein the generated force is greater than the resistance force caused by the medical device acting on the outer tubular member.

Once the stent 2 or device is fully exposed and deployed as shown in FIG. 8, the fluid in the pressure chamber 80 can be removed via the fluid flow port 420 in a suitable manner. For instance, a syringe can withdraw the fluid, i.e. provide negative pressure as shown in FIGS. 9-10. Further, the fluid in the balloon 60 can similarly be withdrawn via the inflation lumen 24. The withdrawal of fluid deflates the piston balloon 60 to a deflated condition as shown in FIGS. 10-11, so that the catheter 100 can be withdrawn from the luminal system of a patient. As the piston balloon 60 deflates, the seal created by the piston balloon in the extended position is annulled. Accordingly, when the piston balloon 60 no longer abuts against the interior surface of the outer member, the fluid between the exterior surface of the inner tubular member 110 and the interior surface of the outer member 120 can move distal to the piston balloon and can further move out the distal end of the catheter, if desired. The progression of the movement of the outer member 120 to deploy the stent seat 2 is depicted in FIGS. 4-11, as described herein.

Additionally, or alternatively, the catheter 100 can include a bellows or bladder component within the pressure chamber to prevent leaks (not shown). For example, the bellows or bladder component can be coupled to the exterior surface of the inner tubular member 110 and is in fluid communication with the fluid flow port 420, wherein fluid introduced through the fluid flow port 420 expands the bellows component to assist in retracting the distal section of the outer member.

In accordance with another aspect of the disclosed subject matter, spacer elements (not shown) can be provided within the pressure chamber 80. The spacer elements can prevent the outer member 120, proximal seal 720 and distal seal 620, if provided, from being collapsed during delivery and storage of the catheter. The spacer elements can also reduce the amount of fluid needed to retract the outer member. The spacer elements can be made of any of a variety of suitable shapes and materials, such as ring members having diameters corresponding to the inner and outer diameters of the inner and outer members, respectively.

If desired, a bumper or stop member can be provided to prevent the distal end of the outer member from being retracted proximally beyond the piston balloon. For example, and as shown in FIG. 4, the catheter 100 can include a stop 710 secured to the inner tubular member 110. The stop 710 is disposed distal to the pressure chamber 80 and proximal to the medical device to be delivered, e.g. the stent 2. Furthermore, for co-axial configurations, the stop 710 can be configured to seal the fluid lumen 310 with the guidewire lumen 320 extending therethrough. Stop 710 can be made of or include a radiopaque material. The radiopacity thus can provide enhanced visibility for the suitable placement of the catheter at the treatment site such as a radiopaque marker. For example, the marker can be a radiopaque metallic ring, or made of a tungsten loaded polymer for increased softness and flexibility. Other suitable markers known can be used.

In accordance with an embodiment of the disclosed subject matter, a method of deploying a catheter as previously described is provided. Solely for purpose of illustration, reference will be made to the embodiment of FIGS. 4-11. However, the disclosed method is likewise applicable to alternative embodiments of the catheter, such as shown in FIG. 13. As depicted in FIG. 4, the piston balloon 60 is in the deflated condition 62 and the stent 2 is in a compressed position. In FIG. 5, fluid is introduced into the inflation lumen 24 to inflate the piston balloon 60. The piston balloon 60 is in the inflated condition and is in sealing engagement with the interior surface 121 of the outer member 120. A pressure chamber 80 is defined by the proximal seal 720, the piston balloon 60, the exterior surface 111 of the inner tubular member 110, and the interior surface 121 of outer member 120. At this point, the inflation of the piston balloon 60 has not caused movement of the outer member 120 and the stent 2 remains in the first position.

FIG. 6 depicts fluid introduced through the fluid lumen 310 and exiting through the fluid flow port 420 into the pressure chamber 80. The pressure in the pressure chamber 80 has not exceeded the force required to move the proximal seal 720 and thus the stent 2 remains in the first or compressed position.

In FIG. 7, the proximal seal 720 of FIG. 6 has shifted length d in the direction A to a new position represented by proximal seal 720. The starting position of the proximal seal 720 is represented by the dotted lines in FIG. 7. As the proximal seal 720 moves in the direction A, the outer member 120 is urged in direction A and moves generally proportionally. As represented by FIG. 7, the distal section of the outer member 120 moves generally the same length d in the direction of A to partially expose the stent 2. The proximal seal 720 and outer member 120 can be configured to provide a 1:1 ratio of the movement of the outer member 120 and the movement of the proximal seal 720, or other suitable ratios as desired. In FIG. 7, the stent 2 has partially expanded.

FIG. 8 shows a further progression in comparison with FIG. 7. In FIG. 8, the stent 2 has been fully exposed due to the retraction of the distal section of the outer member 120 in the direction A. The retraction corresponds to the extension in length of the pressure chamber 80 as more fluid continues to pressurize the pressure chamber 80. The continued pressurization urges the proximal seal 720 in the direction A, as shown by the new position of the proximal seal at 720. In this embodiment, the proximal seal 720 has shifted a full distance f in relation to the starting position. The full distance f is at least equal to the length of the stent 2 or device to be delivered. The starting position of the proximal seal 720 is represented by the phantom lines. Likewise, the distal section of the outer member 120 has shifted the full distance f, as depicted in FIG. 8. The retraction of the outer member 120 allows for deployment of the stent 2.

As depicted in FIG. 9, once the stent seat 3 is fully exposed and the stent 2 contained therein is released, the fluid from the pressure chamber 80 can be withdrawn. Likewise the fluid from the inflated piston balloon 60 can also be withdrawn, as depicted in FIG. 10. In one embodiment, once the piston balloon 60 is deflated, the fluid remaining between the interior surface of the outer member and the exterior surface of the inner tubular member can be released into the patient.

Once the fluid from the pressure chamber 80 and the piston balloon 60 is withdrawn, the catheter 100 can be removed from the vasculature as the stent 2 remains in the second or expanded position, as depicted in FIG. 11.

Embodiments of the disclosed subject matter allow the pressure chamber to operate with a variety of different suitable pressures. Solely for purpose of illustration, in one embodiment the pressure chamber can handle a positive pressure of up to 750 psi, and a negative pressure of approximately 14 psi.

In accordance with another aspect of the disclosed subject matter, and with reference to FIG. 1, an indeflator 500 can be provided to control the inflation and deflation of the piston balloon and the outer tubular member. A pressure gauge can be provided with the indeflator to monitor the pressure system of the catheter. The indeflator allows for the rapid release of hydraulic pressure to stop or inhibit the deployment of the stent. The indeflator can also be configured to create and/or maintain negative pressure in the catheter. For example, by creating a vacuum, the outer tubular member disclosed herein can be configured to decrease in profile and/or lock in position. The indeflator can have a locking mechanism to maintain negative pressure in the catheter. The indeflator can further create a vacuum that decreases the profile of the catheter. An example of a suitable indeflator is an Atrion indeflator Atrion Medical-55 ATM.

The inner tubular member and outer tubular member each can be a single piece construction, or an assembly of components, and can be made of any suitable material. For example, suitable materials include, but are not limited to, polymer materials such as nylon, urethane, polyurethane, PEEK, PTFE, PVDF, Kynar, PE, HDPE, a trilayer material including L25, Plexar, PEBAX or polyethylene of various suitable densities. Furthermore, at least a portion of the inner tubular member can be constructed of an alloy or metallic material, such as stainless steel hypodermic tubing. Example constructions for the outer member include a single layer of PEEK, Polyimide, or Radel; a trilayer material of L25, Plexar, HDPE; or a braided tube with a PTFE or eTFE liner, a Polyimide middle layer with braiding, and a Pebax 72D or Vestamid outer layer.

It is further contemplated that the inner tubular and outer member can be constructed of other biocompatible material. As such, the inner tubular and outer member of the catheter can be constructed from the above-identified polymers, combinations or blends of these polymers, whether alone or in combination with other materials, or other bioabsorbable materials. The inner tubular member and outer member can also be reinforced by the addition of a strengthening member, such as, for example and not limited thereto, a wire coil. In one embodiment, as depicted in FIG. 4, the inner tubular member 110 is reinforced by the addition of a strengthening member 141 along a length corresponding to the pressure chamber 80, further described herein.

As a further alternative, the inner tubular member and/or the outer member each can be constructed of multiple outer tubular members. The one or more proximal stops can further form a joint for two adjacent outer tubular members. The outer member can also be constructed of a composite comprising a fabrication of several different materials, such as a co-extrusion of different polymers, or a fiber-reinforced composite material such as fiber reinforced resin materials or braided materials. Solely for purpose of illustration, further embodiments can include a braided tube with a PTFE liner, a Polyimide middle layer with braiding and a Pebax 72D outer layer. Additionally, to improve flexibility, helical or spiral member configurations can be used in the construction of the inner and outer members.

The proximal section of the outer member can be formed of any suitable material or composite that allows a seal, when the piston balloon is inflated and/or the pressure chamber is pressurized. Solely for purpose of illustration, the proximal section of the outer member can include an elastic or compliant material that permits the outer member to expand initially upon expansion of the piston balloon but reverts back when the piston balloon is deflated. Alternatively, the proximal section can be made of a non-compliant material, similar to a conventional dilatation balloon, which is folded to allow for collapse to a small profile. Thus, the proximal section of the outer member can be less compliant than the distal section. Furthermore, the outer member can be configured to adjust in collapse of the piston balloon when deflated, such as with a semi-compliant material. Exemplary constructions for the outer tubular member include a single layer of polyimide or PEEK; a trilayer material of L25, Plexar, HDPE; or a braided tube with a PTFE liner, a Polyimide middle layer braiding middle layer, and a Pebax 72D outer layer.

Additionally or alternatively, the outer member can have a rigid inner layer and a flexible outer layer, wherein the rigid layer is made of a material that is dissolvable by a selected fluid medium. The pressure chamber can be pressurized with the fluid medium, dissolving the rigid structure and thereby allowing the flexible outer layer to expand in diameter. The outer member can also be formed of a suitable shape-memory material configured to expand across the pressure chamber when the chamber is filled with a hot fluid. As another alternative, the outer member can have a bi-stable design that transitions from a locked or contracted configuration during delivery to an unlocked or expanded configuration upon increased fluid pressure in the pressure chamber.

The outer member can further be provided with an inner layer attached to or formed with an outer layer. The inner layer or liner can include a lubricious material to facilitate the sliding of the outer member in the proximal direction when the outer member is retracted. For example, different types of polymers such as PTFE or high-density polyethylene (HDPE) can be used for the inner layer. Additionally, other lubricious polymers can be used. The outer layer, as embodied herein, provides sufficient strength to capture the intravascular prosthesis therein, as well as allow movement in the proximal direction A. The multiple layers can be formed separately and adhered or bonded together or co-extruded as a single member.

In further accordance with the disclosed subject matter, the outer member can include a reinforcing layer at the distal end portion corresponding to the location of the stent seat 3 and disposed between the outer layer and the inner layer, such as a braided or coiled material. For example, the reinforcing layer can be provided in the form of a braided stainless steel tube or sheet or the like. The braid can include flattened filaments, as opposed to having filaments with a round cross-section. Alternatively, the reinforcement can be in the form of a tube including woven fabric or appropriately oriented filaments, such as carbon fibers encased in a polymeric matrix. Likewise, such reinforcing fibers could additionally or alternatively be incorporated into inner layer and/or outer layer during the manufacturing process.

In embodiments where the outer member comprises an inner layer, outer layer and a reinforcing layer, the outer member can be formed in at least the following manner by way of example. First, the inner layer is formed through a tubular extrusion process, and disposed about a forming mandrel (not shown). The forming mandrel, as embodied herein, has a shape that corresponds to the desired shape of the inside of the outer member. Next, the reinforcing layer, which can be provided in the form of a stainless steel braid material, is positioned over a predetermined length of inner layer. Next, the outer layer is extruded and positioned over the reinforcing layer. The outer layer can be provided in the form of two separate tubular members that are overlapped slightly at their ends over a reinforcing layer. Each portion of outer layer can be a different material selected to provide a different durometer as described above. The two portions of outer layer can overlap by an amount, such as but not limited to, about 0.1 inches. Next, a sleeve of heat shrinkable material is positioned over the entire outer member assembly. Finally, heat is applied to the assembly. When heat is applied, the heat shrinkable tubing shrinks, and causes the inner layer to fuse with outer layer, trapping the reinforcing layer therebetween. The heating process also causes inner layer to conform to the shape of the forming mandrel. After the assembly cools, the heat shrinkable tubing is cut away, leaving behind the outer member.

In accordance with another embodiment, the outer member can be a multilayer tube or balloon including a flexible layer and a rigid layer having a brittle structure configured to fracture upon expansion. The rigid layer can constrain and axially lock a medical device during shipping, storage and delivery, but can rupture upon initial pressurization of the pressure chamber. Once the rigid layer is broken, the flexible layer can maintain a seal while significantly increasing in diameter over the pressure chamber. The multilayer outer tubular member can have a brittle outer layer and a flexible inner layer. As embodied herein, the distal section of the outer tubular member can be multilayer, and include an outer layer of a non-compliant material.

Additionally, the inner tubular member and/or outer tubular member can be constructed from PE, polypropylene, Kynar, or urethane by an extrusion process using an extruder such as that available any of a number of known suppliers. The materials can be post processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner tubular member and/or outer member can be further coated with any of a variety of materials and techniques to enhance performance if desired, including a number of suitable coatings and coating techniques subject to patent matters owned by Abbott Laboratories such as U.S. Pat. No. 6,541,116, U.S. Pat. No. 6,287,285, and U.S. Pat. No. 6,541,116, the entireties of which are hereby incorporated by reference. For example, possible coating materials include lubricious materials such as Teflon®, and hydrophobic materials such as silicone lubricant dispersion PN 4097, or hydrophilic materials such as hydrogel.

The inner tubular member and/or outer member can have any suitable cross-sectional shape, including elliptical, polygon, or prismatic, although a circular cross-section generally is preferred. The inner tubular member and/or outer member can also have any suitable size and diameter depending upon the desired application. The catheter is suitably sized and configured for delivery within a corresponding body lumen for the intended indication, such as a vasculature for vascular intervention. The inner and outer tubular members can also have any suitable size and diameter depending upon the desired application.

The seals of embodiments of the disclosed subject matter can be formed of any suitable materials. For example and not limited thereto, the seal can be silicon or a rubber such as Buna, EPDM, Viton, or Neoprene. In other embodiments, the seal can be formed of a low durometer rubber having a compressed condition and an expanded condition. The seal can be significantly compressed and deformed in the initial delivery configuration, and later transitioning to the expanded condition when the pressure chamber is pressurized. Alternatively, the seal can be made of a hydrophilic polymer that absorbs fluid in the pressure chamber so as to expand proportionally with the outer member. The proximal seal can comprise an expandable material or composite of materials to match the dimensions of the outer member. For example, the seal can expand in cross-dimension with the outer member to maintain an adequate seal. Thus, as the cross-dimension of the pressure chamber expands, the exposed surface area of the seal also increases, resulting in a proportional increase in retraction force generated at a given fluid pressure within the pressure chamber. Thus, an expanding pressure chamber provides for greater retraction force at a given pressure.

The seal assemblies can further include bushings (not shown) to provide a backing to the seals, as known in the art. In accordance with an aspect of the disclosed subject matter, the bushings can be constructed of any suitable material, including, but not limited to, PEEK, Pebax, HDPE, LDPE, mixtures of HDPE and LDPE, a blend of Nylon L75/L25, and the like. In one embodiment, the bushings comprise a metallic material, combination low density polyethelene, silicon, nitril, soft Pebax 30, or other blends of suitable material, and can furthermore have a coating.

According to an embodiment of the disclosed subject matter, the proximal seal and/or distal seal, if provided, can be formed as a separate member and attached to the corresponding tube member, or can be formed as part of the tubular member. For purposes of illustration and not limited thereto, hydrophilic material can be used for the proximal and/or distal seals. For purposes of illustration and not limited thereto, a suitable hydrophilic material can be used for the seals. For purposes of illustration and not limited thereto, hydrophilic material, such as, but not limited to, HydroMed™, Hydrothane™, Hydak®, can be used for the seals. Seals made of such material can be configured to swell when exposed to an aqueous environment, thus sealing more tightly while maintaining lubricity. The seals can comprise an expandable material or composite of materials to increase accordingly to match the dimensions of the outer tubular member. That is, the seal expands with the outer tubular member to maintain an adequate seal. As the pressure chamber expands, the exposed surface area of the seal also increases, resulting in a proportional increase in retraction force at a given fluid pressure. Thus, an expanding pressure chamber provides for greater retraction force at a given pressure.

Alternatively, the proximal and distal seals can be coated with a hydrophobic layer such as oil or wax or made of hydrophobic material such as a fluorocarbon or olefins like polypropylene to be used with a suitable pressurized fluid. Solely, for purpose of illustration, silicone seals with a Hydromer 2314-172 coating. In one embodiment, O-rings can be used for the seal constructions comprised of silicone, buna, or other suitable elastomers. Furthermore, for purpose of example, but not limited thereto, the seal can include soft tubing such as a low durometer Pebax or Santoprene. Additionally or alternatively, a high viscosity hydraulic fluid can be used to inhibit leaks.

In embodiments of the disclosed subject matter, the inner tubular member and/or outer member can furthermore be manufactured using a variety of known and suitable techniques.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as disclosed in U.S. Pat. No. 7,799,065 to Pappas, which is incorporated in its entirety by reference herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a stent throughout this disclosure, other suitable devices and implants likewise can be delivered using the catheter and system disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A catheter comprising:
an inner tubular member having a length and an exterior surface, the inner tubular member defining a fluid lumen and an inflation lumen therein, the exterior surface defining a fluid flow port in fluid communication with the fluid lumen and located along a region of the inner tubular member;
an outer member having a distal section movable relative to the inner tubular member, the outer member having an interior surface facing the exterior surface of the inner tubular member;
a piston balloon coupled to the inner tubular member distal to the fluid flow port and in fluid communication with the inflation lumen, the piston balloon disposed between the inner tubular member and the outer member, the piston balloon having a deflated condition and an inflated condition, wherein the piston balloon in the inflated condition is configured to sealingly engage the interior surface of the outer tubular member while allowing proximal movement of the outer tubular member relative the inner tubular member;
a proximal seal located proximal to the distal section and proximal to the fluid flow port; and
a pressure chamber defined by the proximal seal, the piston balloon in the inflated position, the exterior surface of the inner tubular member, and the interior surface of outer member, the pressure chamber being in fluid communication with the fluid flow port;
wherein fluid introduced through the inflation lumen inflates the piston balloon to seal against the interior surface of the outer member to define the pressure chamber, and fluid introduced through the fluid flow port and into the pressure chamber applies a force to urge at least the distal section of the outer member in a proximal direction.

2. The catheter according to claim 1, wherein the inner tubular member further comprises a guidewire lumen defined therein.

3. The catheter according to claim 2, wherein the guidewire lumen is defined by a guidewire tube disposed within the fluid lumen.

4. The catheter according to claim 1, further comprising a marker secured to the inner tubular member to seal a distal end of the fluid lumen distal of the fluid flow port.

5. The catheter according to claim 1, wherein the fluid lumen is configured to receive a guidewire, the fluid lumen further comprising proximal and distal guidewire seals to seal around a guidewire disposed therethrough.

6. The catheter according to claim 1, wherein the proximal seal comprises a hydrophobic material.

7. The catheter according to claim 1, further comprising a strengthening member disposed in the inner tubular member along a length corresponding to the pressure chamber.

8. The catheter according to claim 1, wherein the piston balloon comprises an inflatable member made of a non-compliant material.

9. The catheter according to claim 1, wherein the outer member includes a proximal section proximal to the distal section, the piston balloon being disposed proximate the proximal section.

10. The catheter according to claim 9, wherein the proximal section of the outer member is less compliant than the distal section.

11. The catheter according to claim 9, wherein the proximal section of the outer member comprises an outer balloon to define at least a portion of the pressure chamber.

12. The catheter according to claim 9, wherein the proximal section of the outer member includes a different material than the distal section.

13. The catheter according to claim 1, wherein the distal section of the outer member is a multi-layer construction.

14. The catheter according to claim 13, wherein the multi-layer construction includes an outer layer of a non-compliant material.

15. The catheter according to claim 1, wherein the outer member comprises a braided material.

16. The catheter according to claim 1, further comprising a stent seat at a distal end of the inner tubular member and a stent positioned at the stent seat.

17. The catheter according to claim 16, further comprising a marker coupled to the inner tubular member proximal to the stent seat.

18. The catheter according to claim 16, wherein the stent is positioned between the inner tubular member and the outer member, wherein upon proximal movement of the outer member, the stent is exposed.

19. The catheter according to claim 1, wherein the catheter is a rapid exchange catheter.

20. The catheter according to claim 1, further comprising a stop to inhibit axial movement of the outer member in the proximal direction beyond a predetermined distance.

21. The catheter according to claim 1, wherein the proximal seal extends from the interior surface of the outer member toward the exterior surface of the inner tubular member.

22. The catheter according to claim 1, wherein the proximal seal is movable in the proximal direction relative the inner tubular member.

23. The catheter according to claim 1, wherein the proximal seal comprises at least one of hydrophilic material or molded hydrophilic material.

24. The catheter according to claim 1, wherein the outer tubular member includes a proximal end, the proximal end sealing coupled with the inner tubular member to form the proximal seal.

25. The catheter according to claim 1, wherein the force is applied proximally against the interior surface of the outer member to urge the outer member in the proximal direction.

26. The catheter according to claim 1, wherein the proximal seal comprises a collar.

27. The catheter according to claim 1, further comprising an indeflator to control pressure in the pressure chamber.

28. The catheter according to claim 1, wherein the proximal seal extends from the interior surface of the outer member toward the exterior surface of the inner tubular member.

29. A method of deploying a catheter comprising:
providing a catheter comprising
an inner tubular member having a length and an exterior surface, the inner tubular member defining a fluid lumen and an inflation lumen therein, the exterior surface defining a fluid flow port in fluid communication with the fluid lumen and located along a region of the inner tubular member,
an outer member having a distal section movable relative to the inner tubular member, the outer member having an interior surface facing the exterior surface of the inner tubular member,
a piston balloon coupled to the inner tubular member distal to the fluid flow port and in fluid communication with the inflation lumen, the piston balloon disposed between the inner tubular member and the outer member, the piston balloon having a deflated condition and an inflated condition, wherein the piston balloon in the inflated condition is configured to sealingly engage the interior surface of the outer tubular member while allowing proximal movement of the outer tubular member relative the inner tubular member,
a proximal seal located proximal to the distal section and proximal to the fluid flow port, and
a pressure chamber defined by the proximal seal, the piston balloon in the inflated position, the exterior surface of the inner tubular member, and the interior surface of outer member, the pressure chamber being in fluid communication with the fluid flow port;
inflating the piston balloon to the inflated condition by introducing inflation fluid through the inflation lumen; and
pressurizing the pressure chamber by introducing pressurizing fluid through the fluid flow port to apply a force on the proximal seal to urge the outer member in a proximal direction.

* * * * *